(12) United States Patent
Plaumann

(10) Patent No.: US 6,375,460 B1
(45) Date of Patent: Apr. 23, 2002

(54) CAPSULE FOR MIXING AND APPLYING DENTAL CEMENT

(75) Inventor: Manfred Thomas Plaumann, Cuxhaven (DE)

(73) Assignee: VOCO GmbH, Cuxhaven (DE)

( * ) Notice: Subject to any disclaimer, the term of this patent is extended or adjusted under 35 U.S.C. 154(b) by 0 days.

(21) Appl. No.: 09/678,892

(22) Filed: Oct. 4, 2000

(30) Foreign Application Priority Data

Feb. 17, 2000 (EP) .............................................. 00103183

(51) Int. Cl.[7] .............................................. A61C 17/00
(52) U.S. Cl. .............................. 433/80; 433/89; 206/219
(58) Field of Search .............................. 433/80, 89, 90; 206/219; 222/386, 82, 83; 366/602

(56) References Cited

U.S. PATENT DOCUMENTS

| | | | |
|---|---|---|---|
| 3,907,106 A | 9/1975 | Purrmann | 206/219 |
| 4,674,661 A | 6/1987 | Herold | 222/386 |
| RE33,801 E | * 1/1992 | Green | 222/82 |
| 5,172,807 A | 12/1992 | Dragon | 206/219 |
| 5,624,260 A | * 4/1997 | Wilcox et al. | 433/90 |

FOREIGN PATENT DOCUMENTS

| DE | 1 586 866 | 8/1970 |
|---|---|---|
| DE | 23 24 296 C3 | 2/1980 |
| DE | 42 32 062 A1 | 4/1993 |
| DE | 197 00 213 A1 | 7/1998 |
| DE | 298 17 643 U1 | 2/1999 |
| EP | 0 157 121 B1 | 10/1985 |
| EP | 0 291 733 B1 | 11/1988 |

* cited by examiner

Primary Examiner—John J. Wilson
Assistant Examiner—Melba Bumgarner
(74) Attorney, Agent, or Firm—Hahn Loeser + Parks LLP; Stephen L. Grant

(57) ABSTRACT

A capsule for mixing and applying dental cement includes a capsule body having a cylindrical shape, a longitudinal axis and a dispensing end. A mixing chamber is located in the capsule body, and it is designed and arranged to hold dental cement. The mixing chamber has an opening region. A piston is located in the capsule body and in the mixing chamber to be axially displaceable for expelling mixed dental cement through the opening region. An exit opening is located at the dispensing end of the capsule body and in the opening region. A closure cap is designed and arranged to cover the opening region. A clamping device is designed and arranged to rotatably connect the closure cap to the capsule body in the opening region to be in opposite fluid-sealing relationship. An unbent application cannula is fixedly mounted to the closure cap at an angle of approximately 10° to 80° with respect to the longitudinal axis of the capsule body.

19 Claims, 3 Drawing Sheets

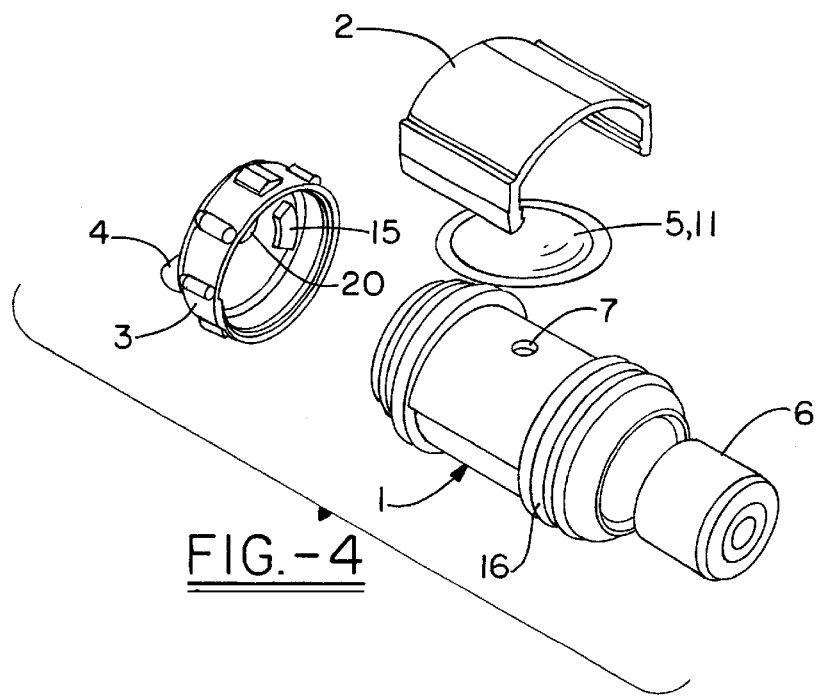
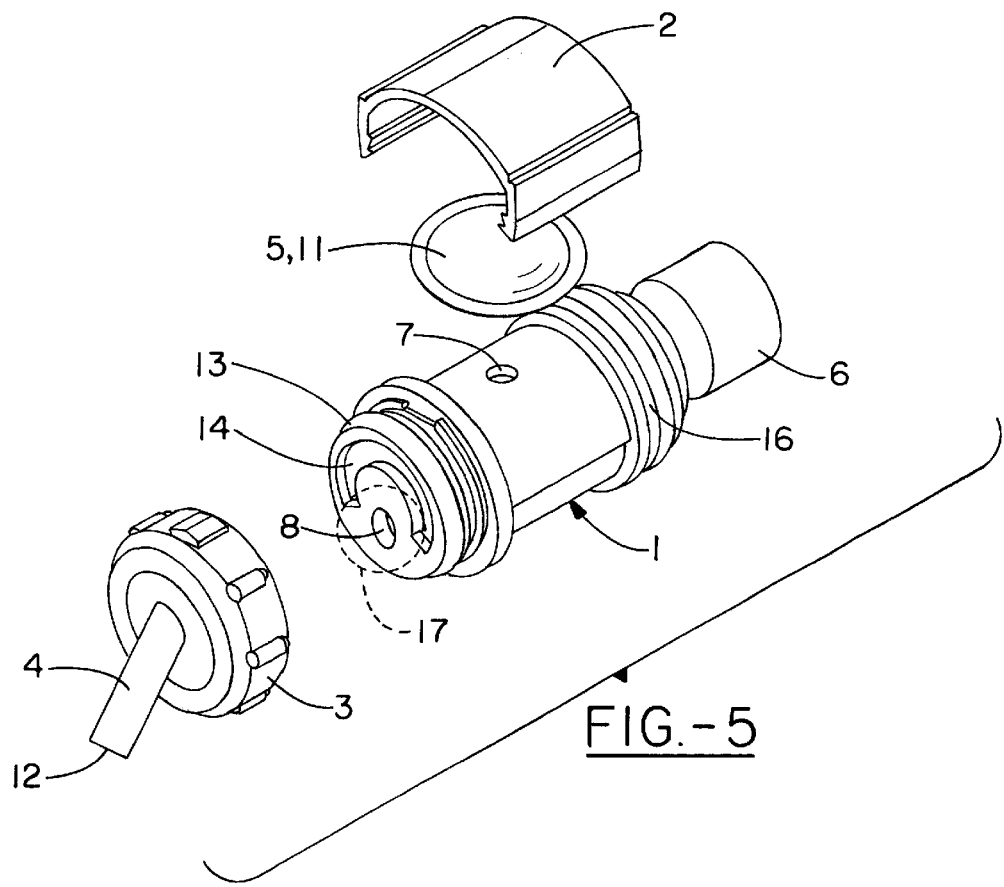

CAPSULE FOR MIXING AND APPLYING DENTAL CEMENT

CROSS REFERENCE TO RELATED APPLICATIONS

This application claims the benefit of European Patent Application Serial Number 00 103 183.0 entitled "Misch- und Applikationskapsel, filed on Feb. 17, 2000.

FIELD OF THE INVENTION

The present invention generally relates to a mixing and application capsule for the production and application of expellable materials, in particular for the production of ready-for-use dental preparations and for application of the preparation directly to the location to be treated.

BACKGROUND OF THE INVENTION

Mixing and application containers are known from German patent Nos. 23 24 296 and 35 66 497.

German patent No. 23 24 296 describes a mixing container having a laterally mounted foil pad and a straight dispensing cannula. The dispensing cannula is closed by a pin which can be withdrawn outwardly. In the case of containers in which the dispensing nozzle is closed by a pin until the time of the dispensing procedure, the problem which arises is that for the dispensing procedure to be implemented the nozzle should admittedly be conical over its length and funnel-shaped in the entry region, but that can give rise to the existence of dead spaces in relation to the pin and the wall of the nozzle. Components can solidify in such spaces during storage or transportation and then do not take part in the mixing procedure. In addition, in the application operation that unmixed component is the first to issue and it prevents or influences proper hardening. Furthermore the pin can be easily removed from the dispensing nozzle, which can result in the content of the capsule being adversely affected. Furthermore waste unavoidably occurs when the closure plug is taken out.

German patent No. 35 66 497 seeks to remedy that disadvantage by virtue of pivotability of the dispensing nozzle. A disadvantage of that design configuration however is the cannula dimensioning which is restricted by virtue of the pivotability involved. As, in the closed condition, the cannula projects beyond the lateral dimensions of the capsule body, the capsule holder of the mixing apparatuses as are described for example in European patent No. 29 17 33 must be provided with recesses or openings in order to permit the capsule to be securely held. A further disadvantage of the limited cannula dimensioning is found in practical use. If the user interrupts the application, the material is frequently observed to continue to come out of the cannula, although no pressure whatsoever is being applied to the application piston.

German patent application No. 15 86 866 describes containers having a plurality of mutually separated chambers, wherein inner and outer discs provided with openings are arranged rotatably. For sealing purposes, those discs are of curved shapes in order to press against each other after assembly.

The known and described apparatuses admittedly endeavour to make the application of a substance which is capable of flow and the admixing thereof more convenient, but they result in complex, expensive and difficult processes and they give rise to special demands in terms of the mixing and application apparatuses. In addition capsule production is also a complex and problematical matter.

SUMMARY OF THE INVENTION

Briefly described, the present invention provides a capsule for mixing and applying dental cement. The capsule includes a capsule body having a cylindrical shape, a longitudinal axis and a dispensing end. A mixing chamber is located in the capsule body, and it is designed and arranged to hold dental cement. The mixing chamber has an opening region. A piston is located in the capsule body and in the mixing chamber to be axially displaceable for expelling mixed dental cement through the opening region. An exit opening is located at the dispensing end of the capsule body and in the opening region. A closure cap is designed and arranged to cover the opening region. A clamping device is designed and arranged to rotatably connect the closure cap to the capsule body in the opening region to be in opposite fluid-sealing relationship. An unbent application cannula is fixedly mounted to the closure cap at an angle of approximately 10° to 80° with respect to the longitudinal axis of the capsule body.

Furthermore, the present invention provides a capsule for mixing at least two components and for applying a ready-for-use dental cement. The components react with each other for the production of the ready-for-use dental cement and for the application of the dental cement directly onto a location to be treated. The capsule includes a capsule body having a cylindrical shape, a longitudinal axis, a dispensing end and an opening. A mixing chamber is located in the capsule body, and it is designed and arranged to hold a first component. The mixing chamber has an opening region. A foil pad is designed and arranged to hold a second component and to close the opening. A clasp portion is designed and arranged to connect the foil pad to the capsule body. A piston is located at a rear end of the capsule body and in the capsule body and in the mixing chamber to be axially displaceable for expelling mixed dental cement through the opening region. An exit opening is located at the dispensing end of the capsule body and in the opening region. A closure cap is designed and arranged to cover the opening region. A clamping device is designed and arranged to rotatably connect the closure cap to the capsule body in the opening region to be in opposite fluid-sealing relationship. An unbent application cannula having an internal contour and an inlet region is fixedly mounted to the closure cap at an angle of approximately 10° to 80° with respect to the longitudinal axis. The application cannula is arranged on the closure cap such that the exit opening and the inlet region of the application cannula can be positioned in mutually superposed relationship and such that the exit opening and the internal contour of the application cannula are of the same dimensions in the inlet region of the application cannula.

The novel capsule is in practice operationally reliable and user-friendly and avoids the disadvantages which are known from the state of the art. Surprisingly the mixing and application capsule according to the invention provides for simple production without problems, for example by means of a plastic injection moulding technology, an uncomplicated configuration, and also safe storage and reliable use, from the point of view of the user. In particular the combination of the essential features of the capsule, as are set forth in the characterising portions of the claims, afford a mixing and application capsule which enjoys the following advantages:

- simple activation for admixing two or more components by lateral pressure applied to the clasp or bar portion;
- mixing is possible in current mixing apparatuses;
- an interruption in the application procedure can be effected without much fuss, the material does not continue to run;

no capsule components project beyond the dimensions of the capsule body, unintended damage to capsule components or the capsule is thereby avoided;

the opened and closed conditions of the capsule can be clearly perceived and can be set by simple rotational movement;

fluid-sealing closure devices provide for secure and reliable storage and actuating conditions and contamination of the components of the mixture is avoided;

the mutually matched dimensioning of the outlet openings permits materials of varying viscosities to be applied without problem;

the producers and suppliers of dental preparations to be mixed require only one basic capsule design for materials of varying viscosities;

application with current apparatuses is possible; and application of the finished mixed preparation directly to the location to be treated, for example into a dental cavity, is possible without any fuss.

The subject-matter of the invention is a capsule for receiving, mixing and application of substances which are capable of flow, that is to say which can be squeezed out. This involves a capsule in which two or more components are mixed in the capsule, the components forming the substance which is capable of flow, and can thereafter be applied directly to the location to be treated.

The novel mixing and application capsule does not suffer from the stated disadvantages known from the prior art. The capsule is easy to operate from the point of view of the user and, in the admixing and application operation, it affords a high level of security, reliability and accuracy. The novel capsule is compact and easy to produce.

Other features and advantages of the present invention will become apparent to one with skill in the art upon examination of the following drawings and the detailed description. It is intended that all such additional features and advantages be included herein within the scope of the present invention, as defined by the claims.

BRIEF DESCRIPTION OF THE DRAWINGS

The invention can be better understood with reference to the following drawings. The components in the drawings are not necessarily to scale, emphasis instead being placed upon clearly illustrating the principles of the present invention. In the drawings, like reference numerals designate corresponding parts throughout the several views.

FIG. 4 is a rear view of individual parts of the mixing and application capsule according to the invention.

FIG. 5 is a front view of individual parts of the mixing and application capsule according to the invention.

DETAILED DESCRIPTION

Figure 1:
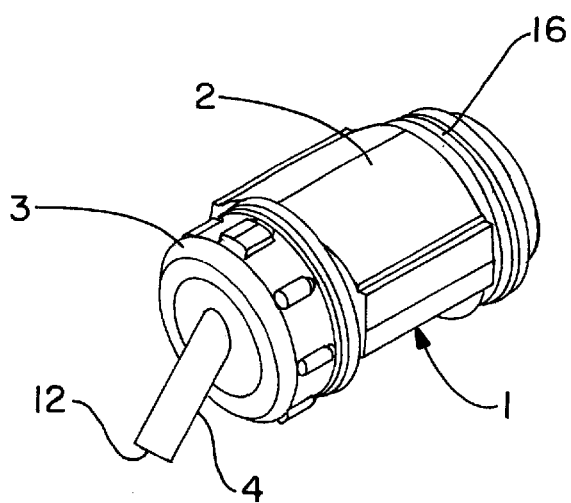
FIG. 1 shows the mixing and application capsule in the closed condition.
Figure 2:
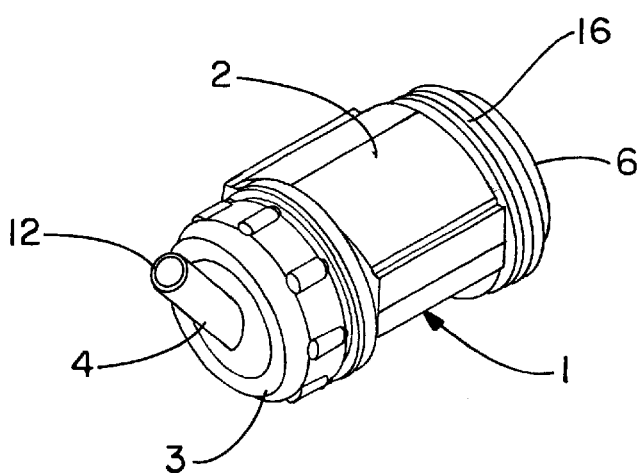
FIG. 2 shows the mixing and application capsule in the opened condition.

Referring now in greater detail to the drawings, FIG. 1 illustrates an external view of an embodiment of a mixing and application capsule which is ready for use, in the closed condition. FIG. 2 shows the same capsule in the opened condition. The capsule includes a capsule body 1 which is cylindrical in shape. Disposed laterally on the capsule body 1 is a clasp or bar portion 2, behind which is concealed a foil pad in which is one of the components to be mixed. The opened and closed condition of the capsule can be set by rotational movement of the closure cap 3 through 180° (FIG. 1 to FIG. 2). If the outlet opening 12 of the application cannula 4 points in the direction of the clasp portion 2 (FIG. 2), it is then possible to perceive the opened condition of the capsule. The application cannula 4 is preferably mounted fixedly to the closure cap 3 at an angle of 50°, relative to the longitudinal axis of the capsule body 1. The application cannula 4 is mounted in laterally displaced relationship with respect to the central axis of the capsule body 1. Provided at the rear end of the capsule is a groove 16 to ensure that the capsule can be accommodated in common application apparatuses.

Figure 3:
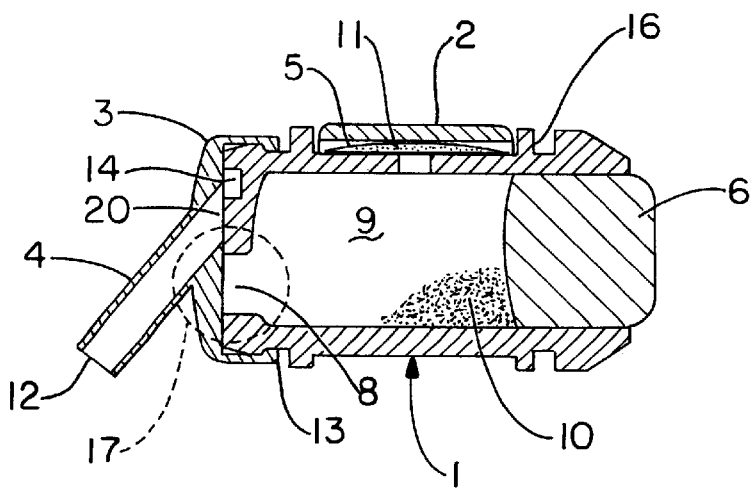
FIG. 3 is a view in longitudinal section of the mixing and application capsule.

FIG. 3 shows the structure and individual components of an embodiment of the mixing and application capsule according to the invention, in longitudinal section.

The mixing and application capsule includes a capsule body 1 which is of a cylindrical shape and whose internal space is used as a mixing space or chamber 9. One or more of the components 10 to be mixed are disposed in the mixing chamber 9. Preferably there is a predetermined dosage of component 10 in powder form in the mixing chamber 9. In particular this involves dental cement constituents in powder form. A further component 11 is disposed in a foil cushion or pad 5 which is held laterally to the capsule body 1 by a bar or clasp portion 2. This generally involves a liquid. Preferably it is a liquid which contributes to setting of the dental cement. The foil pad 5 closes an opening to the mixing chamber (shown at 7 in FIGS. 4 and 5). By virtue of pressure applied to the clasp portion 2 the foil pad 5 bursts at the opening over the mixing chamber and the component to be mixed penetrates from the foil pad 5 into the mixing chamber by way of the opening. That procedure is usually referred to as activation. Usually, common activator apparatuses as are described for example in German utility model No 298 17 643 are used for the activation procedure. Disposed at the rearward end of the capsule is a piston 6 which is axially displaceable for expelling the ready-for-use dental preparation. Disposed at the dispensing end of the capsule body 1, the region of the opening of the mixing chamber, is an exit opening 8 which is closed by a closure cap 3. The region of the opening has a guide groove 14 into which engages a guide pin 15 which is mounted to the closure cap 3 (see FIG. 4). Mounted on the closure cap 3 is an application cannula 4 which is so disposed on the closure cap 3 that the exit opening 8 of the mixing chamber 9 and the inlet region of the application cannula at 20 can be positioned one above the other. The application cannula 4 which is not bent or curved is mounted fixedly to the closure cap 3 at an angle of 10° to 80° preferably at an angle of 50°, which respect to the longitudinal axis of the capsule body 1. The exit opening of the mixing chamber 9 and the internal contour of the application cannula in the inlet region 20 are of the same dimensions so that, when the mixed material is expelled, no material residues can penetrate between the capsule body 1 and the closure cap 3. In the preferred embodiment of the mixing and application capsule the application cannula 4 does not project beyond the lateral dimensions of the capsule body 1, which represents an advantage in terms of handling, in particular in the mixing procedure. The closure cap 3 rotatably co-operates by way of a clamping device 13 with the capsule body in the region 17 of the opening, so that the closure cap 3 and the region of the opening of the capsule body, at 17, are disposed in mutually opposite fluid-tight relationship. That prevents the unintended ingress of troublesome substances or the unintended escape of cement constituents. Furthermore this affords secure reliable stock-keeping and easy handling of the capsules.

As the viscosity of the materials to be applied can be different depending on the respective processing and/or use requirements involved, it may be necessary that the exit opening 8 of the mixing chamber 9 and therewith the inlet region 20 of the application cannula are of different dimensions, in relation to the exit opening of the application cannula, as indicated at 12. In other words, the application cannula 4 is conical over its length and is funnel-shaped in the intake region 20. Any variation in the widths of the openings at 12, 20 is ensured by the configuration according to the invention of the application capsule. This affords a basic capsule structure which is the same for all materials. On the one hand, that makes production of the capsule easier, while on the other hand the user has capsules of the same dimensions, although the capsules contain materials of different viscosities. That means that for example the dentist as the user requires only one and the same application aid, such as for example an application pincer instrument, as is described for example in German patent application No. 197 00 213.

FIGS. 4 and 5 show the individual components of an embodiment according to the invention of the mixing and application capsule as a rear view (FIG. 4) and a front view (FIG. 5) respectively. FIG. 5 shows the guide groove 14 into which engages a guide pin 15 (see FIG. 4) which is mounted on the closure cap 3 so that the closed and the open condition of the capsule is ensured by a rotary movement of the closure cap 3, which is limited to a maximum of 180°. The foil pad 5 closes an opening 7 to the mixing chamber and is held by means of a clasp portion 2. All other components shown in FIGS. 4 and 5 have already been described with reference to FIGS. 1 to 3.

Figure 6A:
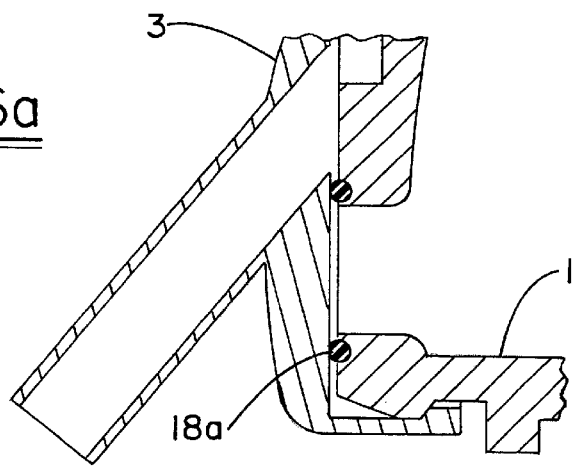
FIGS. 6a and 6b show the region of the opening with closure cap and additional sealing elements.
Figure 6B:
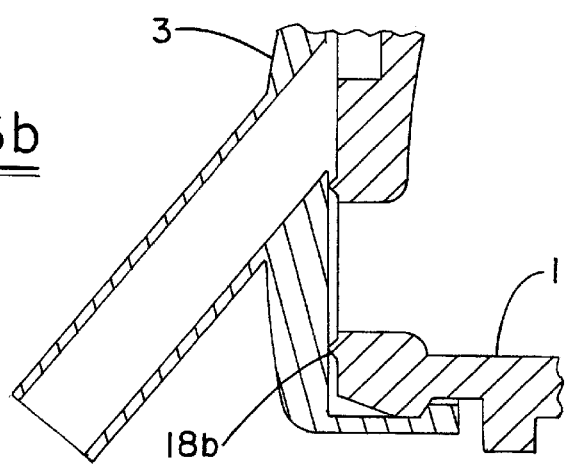

FIGS. 6a and 6b show the region 17 of the opening of a mixing and application capsule according to the invention, with additional sealing elements 18a and 18b which promote the sealing effect of the co-operation of the closure cap 3 and the region 17 of the opening of the capsule. When materials which are sensitive to moisture are disposed in the capsule, that enhanced sealing integrity is essential for the materials to keep properly. FIG. 6a shows that sealing element which is a component of the capsule body 1 in the form of a round seal 18a and FIG. 6b shows it in the form of a bead or ridge seal 18b.

Figure 7:
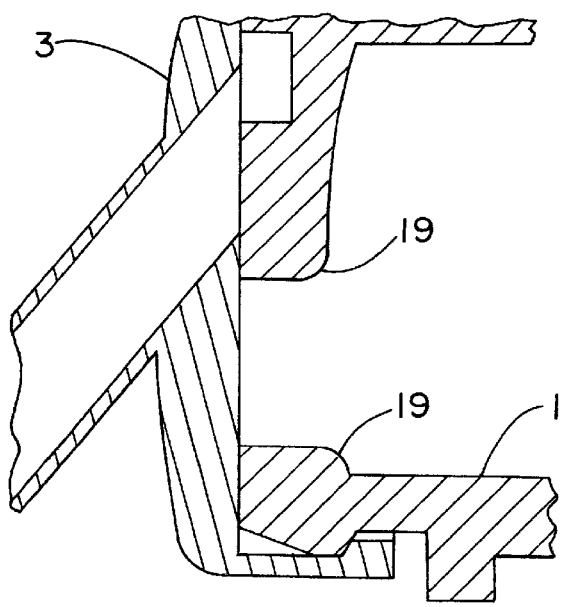
FIG. 7 shows the region of the opening with rounded configurations at the exit opening of the mixing chamber.

FIG. 7 shows rounded configurations at the outlet opening 19 of the mixing chamber. This embodiment is preferred for the viscous materials as this embodiment reduces the flow resistance in the expelling procedure.

Many variations and modifications may be made to the preferred embodiments of the invention without departing substantially from the spirit and principles of the invention. All such modifications and variations are intended to be included herein within the scope of the present invention, as defined by the following claims.

I claim:

1. A capsule for mixing and applying dental cement, comprising:

a capsule body having a cylindrical shape, a longitudinal axis and a dispensing end;

a dental cement mixing chamber being located in said capsule body and being designed and arranged to hold dental cement, said mixing chamber having an opening region;

a piston being located in said capsule body and in said mixing chamber to be axially displaceable for expelling mixed dental cement through the opening region;

an exit opening being located at the dispensing end of said capsule body and in the opening region;

a closure cap fitted to cover the opening region;

a clamping device attached to said closure cap to rotatably connect to said capsule body in the opening region to be in opposite fluid-scaling relationship between an opened and a closed position; and a dental cement application cannula being fixedly mounted to said closure cap such that said exit opening and an inlet region of said application cannula positioned in mutually superimposed relationship in the opened position.

2. The capsule of claim 1, wherein the dental cement is vitreous ionomer cement.

3. The capsule of claim 1, further comprising:

a guide groove being located in the opening region; and a guide pin being mounted to said closure cap, said guide pin being designed and arranged to engage said guide groove and to secure a closed and an opened position of said capsule by a rotary movement of said closure cap being limited to a maximum of approximately 180°.

4. The capsule of claim 1, wherein said application cannula is arranged on said closure cap such that said exit opening and an internal contour of said application cannula are of the same dimensions in the inlet region.

5. The capsule of claim 1, further comprising at least one sealing element being designed and arranged to additionally seal said closure cap with respect to the opening region.

6. The capsule of claim 1, wherein said exit opening and an internal contour of said application cannula are both of an oval configuration.

7. The capsule of claim 1, wherein said exit opening includes rounded edges in the opening region of the mixing chamber.

8. The capsule of claim 1, wherein said application cannula includes an exit opening being of different dimensions than located at the dispensing end of said capsule body.

9. The capsule of claim 1, wherein said application cannula is designed and arranged not to project beyond the lateral dimensions of said capsule body.

10. A capsule for mixing at least two dental cement components and for applying a ready-for-use dental connect, the dental cement components reacting with each other for the production of the ready-for-use dental cement and for the application of the dental cement directly onto a location to be treated, said capsule comprising:

a capsule body having a cylindrical shape, a longitudinal axis, a dispensing end and an opening;

a dental cement mixing chamber being located in said capsule body and being designed and arranged to hold a first dental cement component, said mixing chamber having an opening region;

a foil pad being designed and arranged to hold a second dental cement component and to close said opening;

a clasp portion being designed and arranged to connect said foil pad to said capsule body;

a piston being located at a rear end of said capsule body and in said capsule body and in said mixing chamber to be axially displaceable for expelling mixed dental cement through the opening region;

an exit opening being located at the dispensing end of said capsule body and in the opening region;

a closure cap fitted to cover the opening region;

a clamping device attached to said closure cap rotatably connect to said capsule body in the opening region to be in opposite fluid-scaling relationship between an opened and a closed position; and a dental cement application cannula having an internal contour and an inlet region and being fixedly mounted to said closure cap, said application cannula being arranged on said closure cap such that said exit opening and the inlet region of said application cannula positioned in mutually superposed relationship and such that said exit opening and the internal contour of said application cannula are of the same dimensions in the inlet region of said application cannula.

11. The capsule of claim 10, wherein the dental cement is vitreous ionomer cement.

12. The capsule of claim 10, further comprising at least one sealing element being designed and arranged to additionally seal said closure cap with respect to the opening region.

13. The capsule of claim 10, wherein said exit opening and the internal contour of said application cannula are both of an oval configuration.

14. The capsule of claim 10, wherein said exit opening includes rounded edges in the opening region of the mixing chamber.

15. The capsule of claim 10, wherein said application cannula includes an exit opening being of different dimensions than located at the dispensing end of said capsule body.

16. The capsule of claim 10, wherein said application cannula is designed and arranged not to project beyond the lateral dimensions of said capsule body.

17. A method of mixing and applying dental cement, said method comprising the steps of: mixing dental cement in a capsule including:

a capsule body having a cylindrical shape, a longitudinal axis and a dispensing end, a dental cement mixing chamber being located in the capsule body and being designed and arranged to hold the dental cement, the mixing chamber having an opening region, an exit opening being located at the dispensing end of the capsule body and in the opening region, a closure cap fitted to cover the opening region, a clamping device attached to the closure cap to rotatably connect the capsule body in the opening region to be in opposite fluid-sealing relationship between an opened and a closed position, a dental cement application cannula being fixedly mounted to the closure cap; and expelling the mixed dental cement through the opening region by axially displacing a piston being located in the capsule body and in the mixing clamber.

18. The method of claim 17, wherein the dental cement is vitreous ionomer cement.

19. A pre-measured storable capsule of dental cement, comprising:

a capsule body having a cylindrical shape, a longitudinal axis and a dispensing end;

a mixing chamber located in the capsule body, having an opening region at the dispensing end;

a pre-measured amount of dental cement disposed in the mixing chamber;

a piston, disposed in said mixing chamber in a fluid-sealing manner opposite the dispensing end and axially displaceable therein for expelling the amount of dental cement through the opening region;

an exit opening located at tile dispensing end of the capsule body in the opening region;

a closure cap covering the opening region, the closure cap having an application cannula mounted thereon, with the cannula aligned with the exit opening when the closure cap is in a first position to permit flow of the cement therethrough and the closure cap is with the exit opening in a fluid-scaling relationship when the cap is in a second position; and a clamp device to connect the closure cap to the capsule body such that the closure cap may be rotated between the first and second positions.

* * * * *